United States Patent
Eastham et al.

(10) Patent No.: US 7,371,705 B2
(45) Date of Patent: May 13, 2008

(54) PHOSPHA-ADAMANTANE(S) CATALYTIC SYSTEM

(75) Inventors: Graham R. Eastham, Co Durham (GB); Paul A. Cameron, Darlington (GB); Robert P. Tooze, Fife (GB); Kingsley J. Cavell, Cardiff (GB); Peter G. Edwards, Vale of Glamorgan (GB); Dennis L. Coleman, Mid Glamorgan (GB)

(73) Assignee: Lucite International UK Limited, Southampton Hampshire (GB)

( * ) Notice: Subject to any disclaimer, the term of this patent is extended or adjusted under 35 U.S.C. 154(b) by 0 days.

(21) Appl. No.: 10/524,023

(22) PCT Filed: Aug. 6, 2003

(86) PCT No.: PCT/GB03/03419

§ 371 (c)(1),
(2), (4) Date: Nov. 17, 2005

(87) PCT Pub. No.: WO2004/014552

PCT Pub. Date: Feb. 19, 2004

(65) Prior Publication Data

US 2006/0106259 A1    May 18, 2006

(30) Foreign Application Priority Data

| Aug. 10, 2002 | (GB) | ................... 0218613.8 |
| Nov. 30, 2002 | (GB) | ................... 0228018.8 |
| Jul. 10, 2003 | (GB) | ................... 0316159.3 |

(51) Int. Cl.
*B01J 31/00* (2006.01)

(52) U.S. Cl. ...................... 502/155; 568/454

(58) Field of Classification Search ............... 564/454; 568/454; 502/155
See application file for complete search history.

(56) References Cited

U.S. PATENT DOCUMENTS

| 4,960,949 | A  * | 10/1990 | Devon et al. ............... 568/454 |
| 6,284,919 | B1 |  9/2001 | Pearson et al. |
| 6,335,471 | B1 |  1/2002 | Eastham et al. |
| 6,476,255 | B1 | 11/2002 | Hadden et al. |
| 6,984,668 | B1 * |  1/2006 | Eastham et al. ............... 516/33 |

FOREIGN PATENT DOCUMENTS

| EP | 0055875 | 7/1982 |
| EP | 0106379 | 4/1984 |
| EP | 0 005 875 | 8/1986 |
| EP | 0227160 | 7/1987 |
| EP | 0235864 | 9/1987 |
| EP | 0274795 | 7/1988 |
| EP | 0282142 | 9/1988 |
| EP | 0386833 | 9/1990 |
| EP | 0441447 | 8/1991 |
| EP | 0489472 | 6/1992 |
| EP | 0495547 | 7/1992 |
| EP | 0495548 | 7/1992 |
| EP | 0499329 | 8/1992 |
| GB | 2006208 | 5/1979 |
| WO | WO 96/19434 | 6/1996 |
| WO | WO 99/47528 | 9/1999 |
| WO | WO 01/10551 | 2/2001 |
| WO | WO 01/68583 | 9/2001 |
| WO | WO 01/72697 | 10/2001 |
| WO | WO 03/070370 | 8/2003 |
| WO | PCT/GB2004/002859 | 7/2004 |

OTHER PUBLICATIONS

U.S. Appl. No. 10/527,920.
U.S. Appl. No. 10/524,034, filed Aug. 4, 2003, Eastham et al.
U.S. Appl. No. 10/536,801, filed Dec. 19, 2005, Eastham et al.

* cited by examiner

*Primary Examiner*—Janet L. Andres
*Assistant Examiner*—Sudhakar Katakam
(74) *Attorney, Agent, or Firm*—Venable LLP; Michael A. Sartori; Marina V. Schneller

(57) ABSTRACT

A catalyst system capable of catalysing the carbonylation of an olefinally unsaturated compound is described. The 5 catalyst system is obtainable by combining: (a) a metal of Group VIB or Group VIII B or a compound thereof; and (b) a bidentate phosphine of general formula (I) $Ad_s(CR^4R^5R^6)_T\ Q^2\text{-}A\text{-}(K,D)Ar(E,Z)\text{-}B\text{-}Q^1(Ad)_u(CR^1R^2R^3)_v$. Ad represents an optionally substituted adamantyl radical bonded to the phosphorous atom via any one of its tertiary carbon atoms. A method of production of the catalyst is also illustrated.

19 Claims, No Drawings

PHOSPHA-ADAMANTANE(S) CATALYTIC SYSTEM

This application is the national stage case of PCT/GB03/03419 filed Aug. 6, 2003, which is relied upon and incorporated by reference herein.

The present invention relates to a novel catalyst system and a process for the carbonylation of ethylenically unsaturated compounds using a novel catalyst system.

The carbonylation of ethylenically unsaturated compounds using carbon monoxide in the presence of an alcohol or water and a catalyst system comprising a Group VIII metal, eg. palladium, and a phosphine ligand eg. an alkyl phosphine cycloalkyl phosphine, aryl phosphine, pyridyl phosphine or bidentate phosphine, has been described in numerous European patents and patent applications, eg. EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable higher reaction rates to be achieved. WO 96/19434 discloses a bridging group in the form of an optionally substituted aryl moiety, linked to the said phosphorous atoms via available adjacent carbon atoms on the said aryl moiety. Such a ligand is more stable and leads to reaction rates which are significantly higher than those previously disclosed and produces little or no impurities for carbonylation of a range of olefinically unsaturated compounds. Each phosphorous atom in the said ligand is also linked to two tertiary carbon atoms. It has now been found that a particular type of tertiary carbon atom is particularly advantageous for carbonylation reactions.

According to a first aspect of the present invention there is provided a catalyst system capable of catalysing the carbonylation of an olefinally unsaturated compound, which catalyst system is obtainable by combining:

(a) a metal of Group VIB or Group VIII B or a compound thereof: and
(b) a bidentate phosphine of general formula (I)

(I)

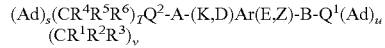

(I)

wherein:

Ar is a bridging group comprising an optionally substituted aryl moiety to which the phosphorus atoms are linked on available adjacent carbon atoms;

A and B each independently represent lower alkylene;

K, D, E and Z are substituents of the aryl moiety (Ar) and each independently represent hydrogen, lower alkyl, aryl, Het, halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $C(S)R^{16}R^{17}$, $SR^{18}$, $C(O)SR^{18}$, or $-J-Q^3(Ad)_w(CR^7(R^8)(R^9))_x$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $C(S)R^{16}R^{17}$, $SR^{18}$ or $C(O)SR^{18}$;

$R^1$ to $R^6$ each independently represent lower alkyl, aryl, or Het;

Ad each independently represent an optionally substituted adamantyl radical bonded to the phosphorous atom via any one of its tertiary carbon atoms, the said optional substitution being by one or more substituents selected from hydrogen, lower alkyl, halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $C(S)R^{16}R^{17}$, $SR^{18}$ or $C(O)SR^{18}$;

$R^{10}$ to $R^{18}$ each independently represent hydrogen, lower alkyl, aryl or Het;

S & U=0, 1 or 2 provided that S+U≧1;
T & V=0, 1 or 2 provided that T+V≦3;
W & X=0, 1 or 2;

$Q^1$, $Q^2$ and $Q^3$ (when present) each independently represent phosphorous, arsenic or antimony and in the latter two cases references to phosphine or phosphorous above should be varied accordingly.

Preferably, the Group VIII B metal is palladium.

Preferably, when K, D, E or Z represent $-J-Q^3(Ad)_w(CR^7(R^8)(R^9))_x$, the respective K, D, E or Z is on the aryl carbon adjacent the aryl carbon to which A or B is connected or, if not so adjacent, is adjacent a remaining K, D, E or Z group which itself represents $-J-Q^3(Ad)_w(CR^7(R^8)(R^9))_x$.

The term "Ar" or "aryl" when used herein, includes five-to-ten-membered; preferably, six-to-ten membered carbocyclic aromatic groups, such as phenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $SR^{18}$, $C(O)SR^{18}$ or $C(S)NR^{16}R^{17}$ wherein $R^{10}$ to $R^{18}$ each independently represent hydrogen, aryl or lower alkyl (Which alkyl group may itself be optionally substituted or terminated as defined below).

By the term "a metal of Group VIB or Group VIIIB" in a compound of formula I we include metals such as Cr, Mo, W, Fe, Co, Ni, Ru, Rh, Os, Ir, Pt and Pd. Preferably, the metals are selected from Ni, Pt and Pd. For the avoidance of doubt, references to Group VIB or VIIIB metals herein should be taken to include Groups 6, 8, 9 and 10 in the modern periodic table nomenclature.

The term "Het", when used herein, includes four-to-twelve-membered, preferably four-to-ten-membered ring systems, which rings contain one or more heteroatoms selected from nitrogen, oxygen, sulphur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) $OR^{10}$, $OC(O)R^{11}$, $C(O)R^{12}$, $C(O)OR^{13}$, $NR^{14}R^{15}$, $C(O)NR^{16}R^{17}$, $SR^{18}$, $C(O)SR^8$ or $C(S)NR^{16}R^{17}$ wherein $R^{10}$ to $R^{18}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term "lower alkyl" when used herein, means $C_1$ to $C_{10}$ alkyl and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $SR^{18}$, $C(O)SR^{18}$, $C(S)NR^{16}R^{17}$, aryl or Het, wherein $R^{10}$ to $R^{18}$ each independently represent hydrogen, aryl or lower alkyl, and/or be interrupted by one or more oxygen or sulphur atoms, or by silano or dialkylsilcon groups. In addition, in the case of substituents on the adamantyl group, more than one lower alkyl group substituent may themselves combine to form a composite group for example a cyclic composite group. An example of an adamantyl substituted in this way is congressane.

Lower alkyl groups or alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R_{14}$, $R^{15}$, $R^{16}$, $R^{17}$, $R^{18}$, K, D, E and Z may represent and with which aryl and Het may be substituted, may, when there is a sufficient number of carbon atoms, be linear or branched, be saturated or unsaturated, be cyclic, acyclic or part cyclic/acyclic, and/or be interrupted by one or more of oxygen or sulphur atoms, or by silano or dialkylsilicon groups, and/or be substituted by one or more substituents selected from halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $SR^{18}$, $C(O)SR^{18}$, $C(S)NR^{16}R^{17}$, aryl or Het wherein $R^{10}$ to $R^{18}$ each independently represent hydrogen, aryl or lower alkyl.

Similarly, the term "lower alkylene" which A, B and J (when present) represent in a compound of formula I, when used herein, includes $C_1$ to $C_{10}$ groups which are bonded to other moieties at least at two places on the group and is otherwise defined in the same way as "lower alkyl".

Halo groups with which the above-mentioned groups may be substituted or terminated include fluoro, chloro, bromo and iodo.

Where a compound of a formula herein contains an alkenyl group, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula (b) I may function as ligands that coordinate with the Group VIB or VIIIB metal or compound thereof (a) to form the compounds for use in the invention. Typically, the Group VIB or VIIIB metal or compound thereof (a) coordinates to the one or more phosphorous, arsenic and/or antimony atoms of the compound of formula I.

Preferably, $R^1$ to $R^9$ each independently represent lower alkyl or aryl. More preferably, $R^1$ to $R^9$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^1$ to $R^9$ each independently represent $C_1$ to $C_6$ alkyl, which is optionally substituted as defined herein. Most preferably, $R^1$ to $R^9$ each represent non-substituted $C_1$ to $C_6$ alkyl such as methyl, ethyl, n-propyl, iso-propyl, n-butyl, iso-butyl, tert-butyl, pentyl, hexyl and cyclohexyl.

Alternatively, or additionally, each of the groups $R^1$ to $R^3$, $R^4$ to $R^6$ and $R^7$ to $R^9$ together independently may form cyclic structures such as 1-norbornyl or 1-norbornadienyl. Further examples of composite groups include cyclic structures formed between $R^1$—$R^9$. Alternatively, one or more of the groups may represent a solid phase to which the ligand is attached.

In a particularly preferred embodiment of the present invention $R^1$, $R^4$ and $R^7$ each represent the same lower alkyl, aryl or Het moiety as defined herein, $R^2$, $R^5$ and $R^8$ each represent the same lower alkyl, aryl or Het moiety as defined herein, and $R^3$, $R^6$ and $R^9$ each represent the same lower alkyl, aryl or Het moiety as defined herein. More preferably $R^1$, $R^4$ and $R^7$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$ and $R^8$ each independently represent the same $C_1$-$C_6$ alkyl as defined above; and $R^3$, $R^6$ and $R^9$ each independently represent the same $C_1$-$C_6$ alkyl as defined above. For example: $R^1$, $R^4$ and $R^7$ each represent methyl; $R^2$, $R^5$ and $R^8$ each represent ethyl; and, $R^3$, $R^6$ and $R^9$ each represent n-butyl or n-pentyl.

In an especially preferred embodiment of the present invention each $R^1$ to $R^9$ group represents the same lower alkyl, aryl, or Het moiety as defined herein. Preferably, each $R^1$ to $R^9$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. Most preferably, each $R^1$ to $R^9$ represents methyl.

In the compound of formula I, preferably each $Q^1$, $Q^2$ and $Q^3$ (when present) are the same. Most preferably, each $Q^1$, $Q^2$ and $Q^3$ (when present) represents phosphorous.

Preferably, in the compound of formula I, A, B and J (when present) each independently represent $C_1$ to $C_6$ alkylene which is optionally substituted as defined herein, for example with lower alkyl groups. Preferably, the lower alkylene groups which A, B and J (when present) represent are non-substituted. A particular preferred lower alkylene which A, B and J may independently represent is —$CH_2$— or —$C_2H_4$—. Most preferably, each of A, B and J (when present) represent the same lower alkylene as defined herein, particularly —$CH_2$—.

Preferably, in the compound of formula I when K, D, E or Z does not represent -J-$Q^3(Ad)_w(CR^7(R^8)(R^9))_x$, K, D, E or Z represents hydrogen, lower alkyl, phenyl or lower alkylphenyl. More preferably, K, D, E or Z represent hydrogen, phenyl, $C_1$-$C_6$ alkylphenyl or $C_1$-$C_6$ alkyl, such as methyl, ethyl, propyl, butyl, pentyl and hexyl. Most preferably, K, D, E and/or Z represents hydrogen.

Preferably, in the compound of formula I when K, D, E and Z together with the carbon atoms of the aryl ring to which they are attached do not form a phenyl ring, K, D, E and Z each independently represent hydrogen, lower alkyl, phenyl or lower alkylphenyl. More preferably, K, D, E and Z each independently represent hydrogen, phenyl, $C_1$-$C_6$ alkylphenyl or $C_1$-$C_6$ alkyl, such as methyl, ethyl, propyl, butyl, pentyl and hexyl. Even more preferably, K, D, E and Z represent the same substituent. Most preferably, they represent hydrogen.

Preferably, in the compound of formula I when K, D, E or Z does not represent $-J-Q^3(Ad)_w(CR^7(R^8)(R^9))_x$, and K, D, E and Z together with the carbon atoms of the aryl ring to which they are attached do not form a phenyl ring, each of K, D, E and Z represent the same group selected from hydrogen, lower alkyl, aryl, or Het as defined herein; particularly hydrogen or $C_1-C_6$ alkyl (more particularly unsubstituted $C_1-C_6$ alkyl) especially hydrogen.

Preferably, in the compound of formula I when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $SR^{18}$, $C(O)SR^{18}$ or $C(S)NR^{16}R^{17}$ wherein $R^{10}$ to $R^{18}$ each independently represent hydrogen or lower alkyl (which alkyl group may itself be optionally substituted or terminated as defined herein). More preferably, the phenyl ring is not substituted by any substituents i.e. it bears hydrogen atoms only.

Preferred compounds of formula I include those wherein:

A and B each independently represent unsubstituted $C_1$ to $C_6$ alkylene;

K, D, Z and E each independently represent hydrogen, $C_1-C_6$ alkyl, phenyl, $C_1-C_6$ alkylphenyl or $-J-Q_3(Ad)_w(CR^7(R^8)(R^9))_x$ where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl.

$R^1$ to $R^9$ each independently represent $C_1$ to $C_6$ alkyl, phenyl or $C_1$ to $C_6$ alkylphenyl.

Further preferred compounds of formula I include those wherein:

A and B both represent —$CH_2$— or —$C_2H_4$—, particularly —$CH_2$—;

K, D, Z and E each independently represent hydrogen, $C_1-C_6$ alkyl phenyl or $C_1-C_6$ alkyl or $-J-Q_3(Ad)_w(CR^7(R^8)(R^9))_x$ where J is the same as A; or two of K, D, E and Z together with the carbon atoms of the aryl ring to which they are attached form an unsubstituted phenyl ring;

$R^1$ to $R^9$ (when present) each independently represent $C_1$ to $C_6$ alkyl and $S+U \geq 3$;

Still further preferred compounds of formula I include those wherein:

$R^1$ to $R^9$ (when present) are the same and each represents $C_1$ to $C_6$ alkyl, particularly methyl and $S+U \geq 3$.

Still further preferred compounds of formula I include those wherein:

K, D, Z and E are each independently selected from the group consisting of hydrogen or $C_1$ to $C_6$ alkyl, particularly where each of K, D, Z and E represent the same group, especially where each of K, D, Z and E represent hydrogen; or K represents —$CH_2-Q^3(Ad)_w(CR^7(R^8)(R^9))_x$ and D, Z and E are each independently selected from the group consisting of hydrogen or $C_1$ to $C_6$ alkyl, particularly where both D and E represent the same group, especially where D, Z and E represent hydrogen.

Especially preferred specific compounds of formula I include those wherein:

each $R^1$ to $R^6$ is the same and represents methyl or $S+U=2$;

A and B are the same and represent —$CH_2$—;

K, D, Z and E are the same and represent hydrogen.

Especially preferred specific compounds of formula I include those wherein Ad is joined to $Q_1$ or $Q_2$ at the same position in each case. Preferably, $S \geq 1$ and $u \geq 1$, more preferably, $S=2$ and $u \geq 1$ or vice versa, most preferably S & U=2.

The present invention provides a process for the carbonylation of an ethylenically unsaturated compound comprising contacting an ethylenically unsaturated compound with carbon monoxide and a hydroxyl group containing compound in the presence of a catalyst system as defined in the present invention.

Suitably, the hydroxyl group containing compound includes water or an organic molecule having a hydroxyl functional group. Preferably, the organic molecule having a hydroxyl functional group may be branched or linear, and comprises an alkanol, particularly a $C_1-C_{30}$ alkanol, including aryl alkanols, which may be optionally substituted with one or more substituents selected from lower alkyl, aryl, Het, halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $C(S)R^{16}R^{17}$, $SR^{18}$ or $C(O)SR^{18}$ as defined herein. Highly preferred alkanols are $C_1-C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of ethylenically unsaturated compound to be carbonylated. Thus the alcohol may serve as the reaction solvent as well, although, if desired, separate solvents may also be used.

It will be appreciated that the end product of the reaction is determined at least in part by the source of hydroxyl group containing compound used. If water is used as the hydroxyl group containing compound then the end product is the corresponding carboxylic acid, whereas use of an alkanol produces the corresponding ester.

In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compound to hydroxyl group containing compound may vary between wide limits and suitably lies in the range of 1:0.1 to 1:10, preferably from between 2:1 to 1:2 and up to a large excess of hydroxyl group containing compounds when the latter is also the reaction solvent such as up to a 50:1 excess of hydroxyl group containing compounds.

The amount of the catalyst of the invention used in the carbonylation process of the ethylenically unsaturated compound is not critical. Good results may be obtained when, preferably, the amount of Group VIB or VIIIB metal is in the range $10^{-7}$ to $10^{-1}$ moles per mole of ethylenically unsaturated compound, more preferably, $10^{-6}$ to $10^{-2}$ moles, most preferably $10^{-5}$ to $10^{-2}$ moles per mole of ethylenically unsaturated compound. Preferably, the amount of bidentate compound of formula I to unsaturated compound is in the range $10^{-7}$ to $10^{-1}$, more preferably, $10^{-6}$ to $10^{-2}$, most preferably, $10^{-5}$ to $10^{-2}$ moles per mole of ethylenically unsaturated compound.

Suitably, although non-essential to the invention, the carbonylation of an ethylenically unsaturated compound as defined herein may be performed in one or more aprotic solvents. Suitable solvents include ketones, such as for example methylbutylketone; ethers, such as for example anisole (methyl phenyl ether), 2,5,8-trioxanonane (diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds eg. benzene, toluene, ethyl benzene o-xylene, m-xylene, p-xylene, chlorobenzene, o-dichlorobenzene, m-dichlorobenzene: alkanes, including halo variants of such compounds eg, hexane, heptane, 2,2,3-trimethylpentane, methylene chloride and carbon tetrachloride; nitriles eg. benzonitrile and acetonitrile.

Very suitable are aprotic solvents having a dielectric constant that is below a value of 50, more preferably in the range of 3 to 8, at 298.15 K and $1\times10^5$ $Nm^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1\times10^5$ $Nm^{-2}$, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7. (at 283.2 K), of dimethyladipate is 6.8 (at 293.2 K), of tetrahydrofuran is 7.5 (at 295.2 K), of methylnonanoate is 3.9 (at 293.2 K). A preferred solvent is anisole.

If the hydroxyl group containing compound is an alkanol, an aprotic solvent will be generated by the reaction as the ester carbonylation product of the ethylenically unsaturated compound, carbon monoxide and the alkanol is an aprotic solvent.

The process may be carried out in an excess of aprotic solvent, i.e. at a ratio (v/v) of aprotic solvent to hydroxyl group containing compound of at least 1:1. Preferably, this ratio ranges from 1:1 to 10:1 and more preferably from 1:1 to 5:1. Most preferably the ratio (v/v) ranges from 1.5:1 to 3:1.

Despite the aforegoing it is preferred that the reaction is carried out in the absence of any external added aprotic solvent ie. an aprotic solvent not generated by the reaction itself.

The catalyst compounds of the present invention may act as a "heterogeneous" catalyst or a "homogeneous" catalyst. By the term "homogeneous" catalyst we mean a catalyst, i.e. a compound of the invention, which is not supported but is simply admixed or formed in-situ with the reactants of the carbonylation reaction (e.g. the vinyl acetate compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 $m^2/g$, a total pore volume in the range of from 0.1 to 4.0 cc/g and an average particle size in the range of from 10 to 500 μm. More preferably, the surface area is in the range of from 50 to 500 $m^2/g$, the pore volume is in the range of from 0.5 to 2.5 cc/g and the average particle size is in the range of from 20 to 200 μm. Most desirably the surface area is in the range of from 100 to 400 $m^2/g$, the pore volume is in the range of from 0.8 to 3.0 cc/g and the average particle size is in the range of from 30 to 100 μm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula I, for example a substituent K, D, Z and E of the aryl moiety, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depend upon the ethylenically unsaturated compound and the groups of the support. For example, reagents such as carbodiimides, 1,1'-carbonyldiimidazole, and processes such as the use of mixed anhydrides, reductive amination may be employed.

According to a further aspect, the present invention provides the use of the process of any aspect of the invention wherein the catalyst is attached to a support.

Particularly preferred is when the organic groups $R^1$, $R^2$, $R^3$, $R^4$, $R^5$, $R^6$, $R^7$, $R^8$ and $R^9$ when associated with their respective carbon atom form composite groups which are at least as sterically hindering as t-butyl. Steric hindrance in this context is as discussed at page 14 et seq of "Homogenous Transition Metal Catalysis—A Gentle Art", by C Masters, published by Chapman and Hall 1981. These steric groups may be cyclic, part-cyclic or acyclic. When cyclic or part cyclic, the group may be substituted or unsubstituted or be saturated or unsaturated. The cyclic or part cyclic groups may contain, including the tertiary carbon atom, from $C_4$-$C_{30}$, more preferably $C_6$-$C_{20}$, most preferably $C_{10}$-$C_{15}$ carbon atoms in the cyclic structure. The cyclic structure may be substituted by one or more substituents selected from halo, cyano, nitro, $OR^{10}$, $OC(O)R^{11}$, $C(O)R^{12}$, $C(O)OR^{13}$, $NR^{14}R^{15}$, $C(O)NR^{16}R^{17}$, $SR^{18}$, $C(O)SR^{18}$, $C(S)NR^{16}R^{17}$, aryl or Het, wherein $R^{10}$ to $R^{18}$ each independently represent hydrogen, aryl or lower alkyl, and/or be interrupted by one or more oxygen or sulphur atoms, or by silano or dialkylsilcon groups.

The bridging group Ar is an aryl moiety, eg. a phenyl group, which may be optionally substituted, provided that the two phosphorus atoms are linked to adjacent carbon atoms, eg. at the 1 and 2 positions on the phenyl group. Furthermore, the aryl moiety may be a fused polycyclic group eg. naphthalene, biphenylene or indene.

Examples of suitable bidentate ligands are 1,2 bis(diadamantylphosphinomethyl)benzene and 1,2 bis(diadamantylphosphinomethyl)naphthalene. Additionally, the bidentate phosphine may be bonded to a suitable polymeric substrate via at least one of the bridging group Ar, the linking group A or the linking group B.

The amount of bidentate ligand used can vary within wide limits. Preferably, the bidentate ligand is present in an amount such that the ratio of the number of moles of the bidentate ligand present to the number of moles of the Group VIB or VIIIB metal present is from 1 to 50 eg. 1 to 10 and particularly from 1 to 5 mol per mol of metal. More preferably, the mol:mol range of compounds, of formula I to Group VIIIB metal is in the range of 1:1 to 3:1, most preferably in the range of 1:1 to 1.25:1. Conveniently, the possibility of applying these low molar ratios is advantageous, as it avoids the use of an excess of the compound of formula I and hence minimises the consumption of these usually expensive compounds. Suitably, the catalysts of the invention are prepared in a separate step preceding their use in-situ in the carbonylation reaction of an ethlenically unsaturated compound.

Conveniently, the process of the invention may be carried out by dissolving the Group VIB or VIIIB metal or compound thereof as defined herein in a suitable solvent such as one of the hydroxyl group containing compounds or aprotic solvents previously described (a particularly preferred solvent would be the ester or acid product of the specific carbonylation reaction eg. Methyl propionate for ethylene carbonylation) and subsequently admixing with a compound of formula I as defined herein.

The carbon monoxide may be used in the presence of other gases which are inert in the reaction. Examples of such gases include hydrogen, nitrogen, carbon dioxide and the noble gases such as argon.

Suitable Group VIB or VIIIB metals or a compound thereof which may be combined with a compound of formula I include cobalt, nickel, palladium, rhodium and platinum. Preferably, the Group VIIIB metal is palladium or a compound thereof. Suitable compounds of such Group VIB or VIIIB metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zero valent palladium complexes particularly those with labile ligands, e.g. triphenylphosphine or alkenes such as dibenzylideneacetone or styrene or tri(dibenzylideneacetone)dipalladium may be used.

The anion may be derived from or introduced as one or more, of an acid having a pKa measured in aqueous solution at 18° C. of less than 4, more preferably, less than 3, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts, other than unsubstituted carboxylates, listed supra.

The quantity of anion present is hot critical to the catalytic behaviour of the catalyst system. The molar ratio of anion to palladium may be from 1:1 to 500:1, preferably from 2:1 to 100:1 and particularly from 3:1 to 30:1. Where the anion is provided by a combination of acid and salt, the relative proportion of the acid and salt is not critical. As mentioned, the catalyst system of the present invention may be used homogeneously or heterogeneously. Preferably, the catalyst system is used homogeneously.

The catalyst system of the present invention is preferably constituted in the liquid phase which may be formed by one or more of the reactants or by the use of a suitable solvent. The molar ratio of the amount of ethlenically unsaturated compound used in the reaction to the amount of hydroxyl providing compound is not critical and may vary between wide limits, eg. from 0.001:1 to 100:1 mol/mol.

The product of the carbonylation reaction using the ligand of the invention may be separated from the other components by any suitable means. However, it is an advantage of the present process that significantly fewer by-products are formed thereby reducing the need for further purification after the initial separation of the product as may be evidenced by the generally significantly higher selectivity. A further advantage is that the other components which contain the catalyst system which may be recycled and/or reused in further reactions with minimal supplementation of fresh catalyst.

Preferably, the carbonylation is carried out at a temperature of between −10 to 150° C., more preferably 0° C. to 140° C., most preferably 20° C. to 120° C. An especially preferred temperature is one chosen between 80° C. to 120° C. Advantageously, the carbonylation can be carried out at moderate temperatures, it is particularly advantageous to be able to carry out the reaction at room temperature (20° C.).

Preferably, when operating a low temperature carbonylation, the carbonylation is carried out between −30° C. to 49° C., more preferably, −10° C. to 45° C., still more preferably 0° C. to 45° C., most preferably 10° C. to 45° C. Especially preferred is a range of 10 to 35° C.

Preferably, the carbonylation is carried out at a CO partial pressure of between $0.80 \times 10^5$ N.m$^{-2}$-$90 \times 10^5$ N.m$^{-2}$, more preferably $1 \times 10^5$ N.m$^{-2}$-$65 \times 10^5$ N.m$^{-2}$, most preferably $1$-$30 \times 10^5$ N.m$^{-2}$. Especially preferred is a CO partial pressure of 5 to $20 \times 10^5$ N.m$^{-2}$.

Preferably, a low pressure carbonylation is also envisaged. Preferably, when operating a low pressure carbonylation the carbonylation is carried out at a CO partial pressure of between, 0.1 to $5 \times 10^5$ N.m$^{-2}$, more preferably 0.2 to $2 \times 10^5$ N.m$^{-2}$, most preferably 0.5 to $1.5 \times 10^5$ N.m$^{-2}$.

The ethylenically unsaturated compounds may be substituted or non-substituted with groups as defined above for the "aryl" group above. Suitable ethylenically unsaturated compounds include ethene, propene, hexene, vinyl compounds such as vinyl acetates, heptene, octene, nonene, decene, undecene, dodecene, etc up to $C_{30}$ which may be linear or branched, cyclic or uncyclic or part cyclic and in which the double bond may take any suitable position in the carbon chain and which includes all stereisomers thereof. The range of ethylenically unsaturated compounds extends to dienes.

The use of stabilising compounds with the catalyst system may also be beneficial in improving recovery of metal which has been lost from the catalyst system. When the catalyst system is utilized in a liquid reaction medium such stabilizing compounds may assist recovery of the group VI or ViiiB metal.

Preferably, therefore, the catalyst system includes in a liquid reaction medium a polymeric dispersant dissolved in a liquid carrier, said polymeric dispersant being capable of stabilising a colloidal suspension of particles of the group VI or VIIIB metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group VI or VIIIB metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group VI or VIIIB metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said group VI or VIIIB metal or metal compound.

By substantially stabilise is meant that the precipitation of the group VI or VIIIB metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly (vinylsulphonic acid).

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $PK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group VI or VIIIB metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

The following examples further illustrate the present invention.

EXAMPLE 1

Preparation of 1,2 bis(diadamantylphosphinomethyl)benzene

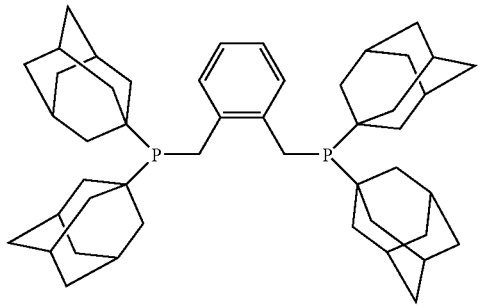

(Method 1)

The preparation of this ligand was carried out as follows.

1.1 Preparation of (1-Ad)$_2$P(O)Cl

Phosphorous trichloride (83 cm$^3$, 0.98 mol) was added rapidly via cannula to a combination of aluminium chloride (25.0 g, 0.19 mol) and adamantane (27.2 g, 0.20 mol) affording a tan suspension. The reaction was heated to reflux. After 10 mins, a yellow-orange suspension was formed. The reaction was refluxed for a total of 6 h. The excess PCl$_3$ was removed by distillation at atmospheric pressure (BP 75° C.). On cooling to ambient temperature, an orange solid was formed. Chloroform (250 cm$^3$) was added yielding an orange suspension, which was cooled to 0° C. Water (150 cm$^3$) was added slowly: initially the suspension viscosity increased, but on full addition of water the viscosity lessened. From this point the reaction was no longer kept under an atmosphere of Ar. The suspension was Buchner filtered to remove the yellow-orange solid impurity. The filtrate consisted of a two phase system. The lower phase was separated using a separating funnel, dried over MgSO$_4$ and Buchner filtered. The volatiles were removed via rotary evaporation, drying finally in-vacuo, affording an off-white powder. Yield 35.0 g, 99%. $^{31}$P NMR: δ=85 ppm, 99% pure. FW=352.85.

1.2 Preparation of (1-Ad)$_2$PH

LiAlH$_4$ (2.54 g, 67.0 mmol) was added over 90 minutes to a chilled (−10° C.) solution of (1-Ad)$_2$P(O)Cl (10.00 g, 28.3 mmol) in THF. (120 cm$^3$). The reaction was allowed to warm to ambient temperature then stirred for 20 h. The grey suspension was cooled to −10° C. HCl (aq., 5 cm$^3$ c. HCl in 50 cm$^3$ degassed water) was added slowly via syringe (initially very slowly due to exotherm of reaction), yielding a two phase system, with some solid material in the lower phase. Further HCl (~5 cm$^3$ c. HCl) was added to improve the separation of the layers. The upper phase was removed via flat ended cannula, dried over MgSO$_4$ and filtered via cannula. The volatiles were removed in-vacuo affording the product as a white powder, isolated in the glovebox. Yield 6.00 g, 70%. $^{31}$=17 ppm, 100% pure. FW=302.44.□P NMR:

1.3 Preparation of (1-Ad)$_2$PCl

A solution of Ad$_2$PH (10.5 g, 34.7 mmol) and DBU (6.12 cm$^3$, 40.9 mmol) in toluene (250 cm$^3$) was chilled to −10° C. Phosgene solution (30.0 cm$^3$, 56.7mmol, was added slowly via cannula; transferring via a measuring cylinder. This afforded a highly viscous pale yellow suspension. Additional toluene (100 cm$^3$) was added via cannula to lessen the viscosity and ease the stirring. The reaction was filtered via cannula affording a yellow filtrate. The residue was washed with additional toluene (2×100 cm$^3$) and the washings combined with the original filtrate. The volatiles, were removed in-vacuo affording a pale yellow solid, which was washed with pentane (2×30 cm$^3$, washings practically colourless). The product was dried in-vacuo and isolated in the glovebox as a lemon yellow powder. Yield 7.84 g, 67%. $^{31}$P=139 ppm, 99+ % pure. FW=336.88.□NMR:

1.4 Preparation of 1,2-bis(di-1-adamantylphosphinomethyl)benzene

1.4.1 Preparation of DI-SODIO-ORTHO-XYLENE(DISOD)

Bu"Li (2.5 M in hexanes, 11.28 cm$^3$, 28.2 mmol) was added dropwise via syringe over 15 minutes to a stirred suspension of NaOBu$^t$ (crushed, 2.71 g, 8.2 mmol), o-xylene (1.15 cm$^3$, 9.4 mmol) and N,N,N',N'-tetramethyl ethylene diamine (TMEDA) (4.26 cm$^3$, 28.2 mmol) in heptane (100 cm$^3$). The reaction was heated at 60° C. for 2 h, then allowed to cool/settle, affording a bright orange solid (DISOD) and pale yellow solution. The solution was removed via cannula filtration and the solid washed with additional heptane (50 cm$^3$) and dried in-vacuo. 90% yield assumed, 8.47 mmol.

1.4.2 Reaction of DI-SODIO-ORTHO-XYLENE with 2 equiv (1-Ad)$_2$PCl

A suspension of DISOD (8.47 mmol) in Et$_2$O (100 cm$_3$) was prepared at −78° C. A suspension of Ad$_2$PCl (5.70 g, 16.9 mmol) in Et$_2$O (120 cm$^3$) was stirred rapidly at −78° C. and added via wide-bore cannula to the DISOD suspension. The reaction was allowed to warm to ambient temperature and stirred for 18 h, affording a pale yellow turbid solution. Water (degassed, 100 cm$^3$) added via cannula affording a two phase system, with a great deal of white solid present (product) due to the low solubility of this material. The upper phase (Et$_2$O) was removed via cannula. The solid in the aqueous phase was extracted using dichloromethane (200 cm$^3$), forming two clear phases. The lower phase (CH$_2$Cl$_2$) was removed via cannula and combined with the original Et$_2$O phase. The volatiles were removed in-vacuo yielding a slightly sticky solid. The solid was washed with pentane (200 cm$^3$) with attrition being performed, the washings being removed via cannula filtration. The white solid was dried in-vacuo and isolated in the glovebox as a friable white powder. Yield 3.5 g, 59%. FW=707.01.

$^{31}$P {$^1$H}NMR data:—δ 24 ppm.

$^1$H NMR data:—(400 MHz, CDCl$_3$, 298 K) δ 7.59-7.50 (m, 2H, Ar—H), 7.09-6,99 (m, 2H, Ar—H), 3.01 (d, 4H, $^2$J$_{PH}$=3.2 Hz, CH$_2$), 2.07-1.57 (m, 60H, C$_{10}$H$_{15}$) ppm.

$^{13}$C {$^1$H} NMR data:—(100 MHz, CDCl$_3$, 298 K) δ 139.4 (dd, J$_{PC}$=10.7 Hz, J$_{PC}$=2.3 Hz, Ar—C), 131.0 (d, J$_{PC}$=16.8 Hz, Ar—C), 125.0 (s, Ar—C), 41.1 (d, $^2$J$_{PC}$=10.7 Hz, Ad-C$^2$), 37.2 (s, Ad-C$^4$), 36.9 (d, $^1$J$_{PC}$=22.9 Hz, Ad-C$_1$), 28.8 (d, $^3$J$_{PC}$=7.6 Hz, Ad-C$^3$), 22.0 (dd, $^1$J$_{PC}$=22.9 HZ, $^4$J$_{PC}$=3.1 Hz, CH$_2$).

EXAMPLE 2

Preparation of 1,2 bis(diadamantylphosphinomethyl)benzene (Method 2)

2.1 Di-1-adamrantyl phosphinic chloride. Phosphorus trichloride (83 cm³, 0.98 mol) was added rapidly via cannula to a mixture of (freshly sublimed) AlCl₃ (26.66 g, 0.2 mol) and adamantane (27.2 g, 0.20 mol) to afford a buff coloured suspension. Upon reflux and stirring of the solution a tangerine coloured suspension was observed. Upon further reflux the suspension darkened to reach a deep orange colour. The suspension was refluxed for a total of 18 hrs. Excess phosphorus trichloride was then removed via distillation (BP: 75° C.) to afford an orange solid. Upon cooling to ambient temperature, chloroform (250 cm³) was added to regenerate the orange suspension. The suspension was then cooled to 0° C. and water (150 cm³) was added gradually via syringe. From this point onward it is unnecessary to employ an inert atmosphere. The orange suspension was buchner filtered (with celite) to remove the orange solid impurity. The lower (chloroform) phase of the filtrate was then separated with a separating funnel and dried with magnesium sulphate. After a second buchner filtration (with celite), the solvent was removed from the suspension via rotary evaporation, to afford an off white solid as the product. Yield: 34.89 g, 99%, 99% pure. FW: 352.85. $^{31}$P NMR: δ: 86 ppm (s).

2.2 Di-1-adamantyl phosphine. LiAlH₄ (3.5 g, 74 mmol) was added over 2 hrs to a cooled solution (0° C.) of di-1-adamantyl phosphinic chloride (16 g, 45 mmol) in THF (250 cm³). The reaction was then allowed to warm to ambient temperature and was stirred for 20 hrs. The grey suspension was then cooled (0° C.) and HCl (75 cm³, 1M) was slowly added via syringe, to afford a two phase system with some solid present in the lower phase. Concentrated HCl (8 cm³, 11M) was then added to improve the separation of the two layers. The (upper) THF phase was removed via cannula and dried over magnesium sulphate. After filtration via cannula, the volatiles were removed in-vacuo to afford the product as a white solid. Yield: 9.1 g, 67%, 95% pure. FW: 302.44. $^{31}$P NMR: δ: 18 ppm (s).

2.3 (Di-1-adamantyl phosphine)trihydro boron. Borane (THF) adduct (10 cm³, 10 mmol) was added to stirred solution of di-1-adamantyl phosphine (1.36 g, 4.5 mmol) in THF (30 cm³). Stirring for a further 5 hrs afforded a slightly turbid solution. The volatiles were then removed in-vacuo to yield the product as a pure white solid. Yield: 1.39 g, 98%, 99% pure. FW: 315.25. $^{31}$P NMR: δ 41 ppm (d, $J_{PB}$ 64 Hz).

2.4 Synthesis of 1,2 bis(di-1-adamantylphosphor(borane) methyl)benzene via deprotonation with $^{sec}$BuLi and reaction with αα dichloro o-xylene. To a stirred, cooled (−78°) THF solution (60 cm³) of di-1-adamantyl phosphine trihydroboron (5 g, 15.8 mmol), was slowly added (via syringe) $^{sec}$BuLi (12.3 cm³, 16.6 mmol), upon full addition the solution had a noticeable yellow colouration. The solution was stirred for 30 minutes at −78° and then allowed to warm to room temperature and stir for a further 120 minutes. The solution was then cooled to −78° and a THF solution (20 cm³) of αα dichloro o-xylene was added via cannula. The solution was then allowed to warm to room temperature and stirred for 15 hrs. The volatiles where then removed in-vacuo. No further work up was required as LiCl and excess organics are removed during the deprotection procedure. Yield: 100% 85% pure.

$^{31}$P {$^1$H} NMR (CDCl₃, 298K) δ (d, br) 41 ppm.
$^{11}$B {$^1$H} NMR δ −43 ppm (d, $J_{BP}$ 44 Hz)
$^1$H NMR (CDCl₃, 298K) δ 7.8-7.50 ppm (m,br Ar—H), δ 7.49-7.00 ppm (m, br Ar—H), δ 3.3 ppm (d, CH₂), δ 2.2-1.2 ppm (m, C₁₀H₁₅)

2.5 Synthesis of 1,2-bis(di-adamantylphosphinomethyl)benzene via deprotection of 1,2 bis(di-adamantylphosphor(borane)methyl)benzene with HBF₄.O(ME)₂

Tetrafluoroboric acid dimethyl ether complex (5 equivalents, 12.5 mmols, 1.5 cm³) was added slowly via syringe to a cooled (0° C.) stirred solution of 1,2bis (di-adamantylphosphor(borane)methyl benzene (70 cm³ dichloromethane). The solution was stirred at 0° C. for 1 hour and then allowed to warm to ambient temperature and stir for a further 12 hours. The reaction mixture was then added to a cooled (0° C.) saturated solution (degassed) NaHCO₃ solution (5* excess NaHCO₃) and stirred vigorously for 50 minutes. The organic phase was then extracted with 2*30 cm³ portions of diethyl ether, and added to the DCM extract. The organic layers were then washed with 2×30 cm³ portions of degassed water and dried over MgSO₄. The volatiles were then removed in-vacuo.

$^{31}$P {$^1$H} NMR:δ 26.4 ppm (s).
H$^1$ NMR (CDCl₃, 298K) δ 7.54 ppm (q, Ar—H, $J_{HH}$ 3.4 Hz), 7.0 ppm (q, Ar—H, $J_{HH}$ 3.4 Hz), 3.0 ppm (d, br CH₂) 1.6-2.1 ppm (m, br C₁₀H₁₅).

EXAMPLE 3

Preparation of 1,2 bis(di-3,5-dimethyladamantylphosphinomethyl)benzene (Method 2)

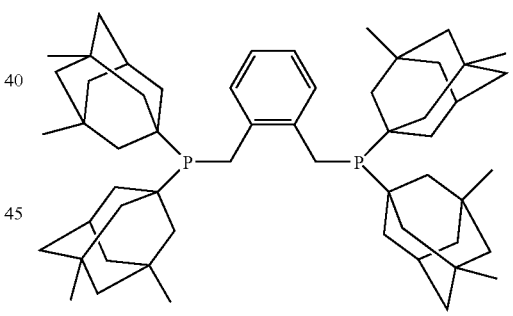

3.1 Di-1-(3,5-dimethyladamantyl)phosphinic chloride was prepared in accordance with the method of example 2.1 except using 1,3 dimethyladamantane 21.7 g (0.132 mol) instead of adamantane, and AlCl₃ (18.5 gg, 0.14 mol). Yield 23.5 g FW: 409.08. $^{31}$P NMR: δ: 87 ppm (s).

3.2 Di-1-(3,5-dimethyladamantyl)phosphine was prepared as per 2.2 above except using 25.0 g Di-1-(3,5-dimethyladamantyl)phosphinic chloride instead of di-1-adamantyl phosphonic chloride Yield 15.7 g FW: 358.58. $^{31}$P NMR: δ: 15.7 ppm (s).

3.3 Di-1-(3,5-dimethyladamantyl)phosphine}trihydro boron was prepared as per 2.3 above except using 10.0 g Di-1-(3,5-dimethyladamantyl)phosphine instead of di-1-adamantyl phosphine. Yield 9.5 g $^{31}$P NMR: δ: 40.5 ppm (br).

3.4 Synthesis of 1,2 bis(di-3,5-dimethyladamantyl(borane)methyl)benzene via deprotonation with $^{sec}$BuLi and reaction with αα dichloro o-xylene was prepared as per 2.4 above except using equimolar amounts of di-3,5-dimethyl adamantyl phosphine trihydroboron instead of di-1-adamantyl phosphine trihydroboron.

3.5 Synthesis of 1,2 bis(di-3,5-dimethyladamantylphosphinomethyl)benzene via deprotection of 1,2 bis(di-3,5-dimethyladamantyl phosphor(borane)methyl)benzene with HBF$_4$.O(ME)$_2$ was prepared as per 1,2 bis(di-1-adamantylphosphinomethyl)benzene (2.5) above except by using equimolar amounts of 1,2 bis(di-3,5-dimethyadamantylphosphor(borane)methyl)benzene instead of 1,2 bis(di-adamantylphosphor(borane)methyl)benzene.

EXAMPLE 4

Preparation of 1,2 bis(di-4-tert-butyladamantylphosphinomethyl)benzene (Method 2)

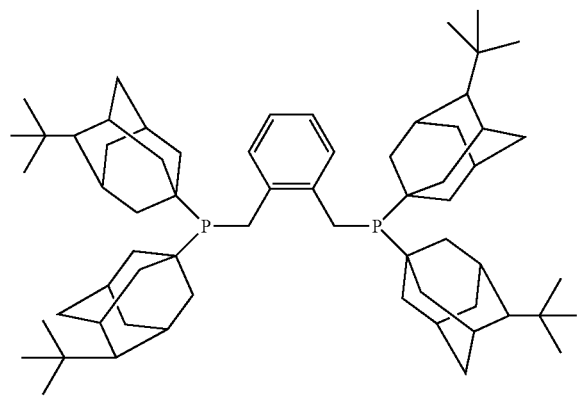

4.1 Di-1-(4-tert-butyladamantyl)phosphinic chloride was prepared as per Di-1-adamantyl phosphinic chloride above except using 4-tert-butyladamantane 25.37 g (0.132 mol) instead of adamantane, and AlCl$_3$ (18.5 gg, 0.14 mol). Yield 22.6 g FW: 464.98. $^{31}$P NMR: δ: 87 ppm (s).

4.2.1 Di-1-(4-tert-butyladamantyl)phosphine was prepared as per Di-1-adamantyl phosphine above except using 13.5 g Di-1-(4-tert-butyladamantyl)phosphinic chloride instead of di-1-adamantyl phosphinic chloride. Yield 9.4 g FW: 414.48. $^{31}$P NMR: δ: 18.62 ppm (s).

4.2.2 Di-1-(4-tert-butyladamantyl)phosphine}trihydro boron was prepared as per Di-1-adamantyl phosphine above except using 10.0 g Di-1-(4-tert-butyladamantyl)phosphine instead of di-1-adamantyl phosphine. Yield 9.5 g $^{31}$P NMR: δ: 41.6 ppm (br).

4.2.3 Synthesis of 1,2 bis(di-4-tert-butyladamantylphosphor(borane)methyl)benzene via deprotonation with $^{sec}$BuLi and reaction with αα dichloro o-xylene was prepared as per 1,2 bis(di-1-adamantylphosphor(borane)methyl)benzene above except using equimolar amounts of di-1-(4-tert-butyladamantyl)phosphine trihydroboron instead of di-1-adamantyl phosphine trihydroboron.

4.3 Synthesis of 1,2 bis(di-4-tert-butyladamantylphosphinomethyl)benzene via deprotection of 1,2 bis(di-4-tert-butyladamantylphosphor(borane)methyl)benzene with HBF$_4$.O(ME)$_2$ was prepared as per 1,2 bis(di-1-adamantylphosphinomethyl)benzene above except 1,2 bis(di-4-tert-butyladamantylphosphor(borane)methyl)benzene was used instead of 1,2 bis(di-adamantylphosphor(borane)methyl)benzene in equimolar amounts.

EXAMPLE 5

Preparation of 1,2 bis(1-adamantyl tert-butyl-phosphinomethyl)benzene (Method 2)

5.1. 1-adamantylphosphonic acid dichloride. This compound was synthesised according to the method of Olah et al (J. Org. Chem. 1990, 55, 1224-1227).

5.2 1-adamantyl phosphine. LiAlH$_4$ (3.5 g, 74 mmol) was added over 2 hrs to a cooled solution (0° C.) of 1-adamantylphosphonic acid dichloride (15 g, 59 mmol) in THF (250 cm$^3$). The reaction was then allowed to warm to ambient temperature and was stirred for 20 hrs. The grey suspension was then cooled (0° C.) and HCl (75 cm$^3$, 1M) was slowly added via syringe, to afford a two phase system with some solid present in the lower phase. Concentrated HCl (8 cm$^3$, 11N) was then added to improve the separation of the two layers. The (upper) THF phase was removed via cannula and dried over magnesium sulphate. After filtration via cannula, the volatiles were removed in-vacuo to afford the product.

5.3 (1-adamantyl-tert-butylphosphine)trihydro boron. nBuLi (20 cm$^3$, 32 mmol 1.6M soln) was added over 1 hour to a cooled solution of 1-adamantyl phosphine (5.0 g 30 mmol) in THF (100 cm$^3$). The solution was allowed to warm to room temperature and stirred for a further 2 hours. The solution was recooled to 0° C. and tert-butylchloride (2.78 g, 30 mmol) was added and stirring continued for a further 16 hours at room temperature. The material was isolated as the borane adduct by addition of Borane (THE) adduct (30 cm$^3$, 30 mmol) followed by removal of the solvent. The material was isolated as a white solid which was a mixture of isomers.

5.4 Synthesis of 1,2 bis(1-adamantyl-tert-butylphosphor (borane)methyl)benzene via deprotonation with $^{sec}$BuLi and reaction with αα dichloro o-xylene. The synthesis was carried out as per 1,2 bis(di-1-adamantylphosphor(borane) methyl)benzene above except equimolar amounts of 1-adamantyl-tert-butyl(phosphine)trihydroboron were used instead of the di-1-adamantyl phosphine trihydroboron.

5.5 Synthesis of 1,2 bis(1-adamantyl-tert-butylphosphinomethyl)benzene via deprotection of 1,2 bis(1-adamantyl-tert-butylphosphor(borane)methyl)benzene with HBF$_4$.O (ME)$_2$. As per 1,2 bis(di-adamantylphosphorinomethyl) benzene except using equimolar amounts of 1,2 bis(1-adamantyl-tert-butylphosphor(borane)methyl)benzene instead of 1,2 bis)(di-adamantylphosphor(borane)methyl) benzene.

EXAMPLE 6

Preparation of 1,2 bis(di-1-diamantanephosphinomethyl)benzene.Diamantane=congressane

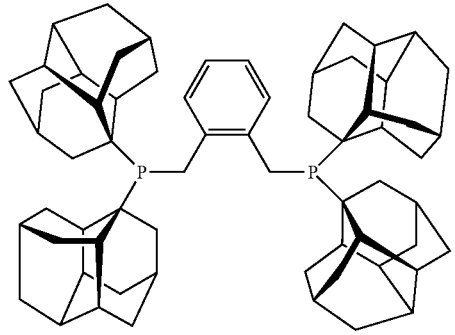

6.1 Diamantane. This was synthesised according to the method of Tamara et. al. Organic Syntheses, CV 6, 378

6.2 Di-1-(diamantane)phosphinic chloride. Prepared as per Di-1-adamantyl phosphinic chloride except using diamantane 20.0 g (0.106 mol) and $AlCl_3$ (16.0 g, 0.12 mol). Yield 25.5 g FW: 456.5. $^{31}P$ NMR: δ: 87 ppm (s).

6.3 Di-1-(diamantane)phosphine. Prepared as per Di-1-adamantyl phosphine except using 25.0 g Di-1-(diamantane) phosphinic chloride. Yield 14.0 g FW: 406. $^{31}P$ NMR: δ: 16.5 ppm (s).

6.4 Di-1-(diamantane)phosphine}trihydro boron. Prepared as per Di-1-adamantyl phosphine trihydro boron except using 15.0 g Di-1-(diamantane)phosphine. Yield 14.5 g. $^{31}P$ NMR: δ: 42.1 ppm (br).

6.5 Synthesis of 1,2 bis(diamantane phosphor(borane) methyl)benzene via deprotonation with $^{sec}BuLi$ and reaction with αα dichloro o-xylene. Prepared as per 1,2 bis(di-1-adamantylphosphor(borane)methyl)benzene except using an equimolar amount of diamantane phosphine trihydroboron instead of di-1-adamantyl phosphine trihydroboron.

6.6 Synthesis of 1,2 bis (diamantanephosphinomethyl) benzene via deprotection of 1,2 bis(diamantane (borane) methyl)benzene with $HBF_4.O(ME)_2$. Prepared as per 1,2 bis(di-1-adamantylphosphinomethyl)benzene except using an equimolar amount of 1,2 bisdiamantinephosphor(borane) methyl)benzene instead of 1,2 bis(di-adamantylphosphor (borane)methyl)benzene.

EXAMPLE 7 (COMPARATIVE)
Preparation of 1,2-bis-(ditertbutylphosphinomethyl)benzene The preparation of this ligand was carried out in the manner disclosed in WO 99/47528 in accordance with example 18.

EXAMPLE 8 (COMPARATIVE)

Preparation of 1,3 bis(diadamantylphosphino)propane

Preparation of 1,3-bis-(di-1-adamantylphosphino)propane (2)

8.1 Preparation of $(1-Ad)_2PLi$

Bu"Li (2.5 M in hexanes, 42.02 cm³, 105.1 mmol) was added dropwise via syringe to a stirred solution of $Ad_2PH$ (10.59 g, 35.0 mmol) in THF (150 cm³). This resulted in a darkening of the solution to yellow and the precipitation of a large quantity of yellow solid, in a mildly exothermic reaction. The reaction was stirred at ambient temperature for 3 h. The volatiles were removed in-vacuo, affording a very pale orange solid. The solid was washed with pentane (2×50 cm³) to remove excess Bu"Li, resulting in the isolation of a white powder (washings orange) which was dried in-vacuo. The yield for this step was assumed to be quantitative, on the basis of previous NMR experiments.

8.2 Reaction of 1,3-dibromopropane with 2 equiv $(1-Ad)_2PLi$ 1,3-dibromopropane (degassed, 1.78 cm³, 17.5 mmol) was added dropwise via syringe to a stirred suspension of $Ad_2PLi$ (35.0 mmol, prepared as above) in THF (150 cm³). Initially a yellow solution was formed, then a great deal of white solid crashed out (product). The volatiles were removed in-vacuo and dichloromethane (300 cm³) added via cannula affording a turbid solution. The turbidity was lost on addition of water (degassed, 100 cm³), a two phase system being formed. The lower phase was removed via cannula filtration. The volatiles were removed in-vacuo, affording a white powder, which was washed with pentane (100 cm³), dried and isolated in the glovebox. Yield 6.45 g, 57%. $^{31}$=24 ppm, 95+ % pure. FW=□P NMR: 644.94.

EXAMPLE 9

Preparation of 1,2-bis(di-1-adamantylphosphinomethyl)benzene palladium (dba)

THF (100 cm³) was added to a combination of ligand (2.05 g, 2.90 mmol) and palladium dba (1.61 g, 2.90 mmol [Pd]) affording a deep red-orange turbid solution. The reaction was stirred for 3 h. The reaction was filtered via cannula, yielding a deep red-orange filtrate and a small quantity of [Pd] residue. The volatiles were removed in-vacuo affording a deep red powdery solid. Pentane (50 cm³) was added via cannula and attrition performed with a spatula, resulting in an orange powder separating out. The amber pentane washings were removed via cannula filtration, and the solid washed with $Et_2O$ at −10° C. (3×50 cm³). The resultant orange powder was dried in-vacuo and isolated in the glovebox. Yield 2.68 g, 88% $^{31}$=46, 42□P NMR: ppm (1:1 ratio), essentially phosphorus pure. FW=1047.73.

EXAMPLE 10

Preparation of 1,3-bis-(di-1-adamantylphosphino)propane palladium (dba)

As in Example 4, except using ligand (1.96 g, 3.04 mmol) and palladium dba (1.69 g, 3.04 mmol [Pd]) in THF (70 cm³). After 3 h, the deep red-orange solution was fairly turbid in appearance; an additional 50 cm³ THF was added to further dissolve the product. The reaction was worked-up as above, except the $Et_2O$ washing was performed at ambient temperature. The solid was isolated in the glovebox as an orange powder. Yield 2.08 g, 69% $^{31}$=42, □P NMR: 38 ppm (1:1 ratio, noisy). FW=985.66.

Experimental

The catalysis experiments were carried out in a magnetically stirred 300 ml glass Buchi autoclave unless otherwise indicated. The activity of the compounds was first tested by generating the catalysts in-situ by reacting two equivalents of ligand with palladium dba (50 mg) in methanol (100 ml) followed by addition of MeSO$_3$H (10 equiv). This solution was charged to the autoclave under an inert atmosphere. The solution was then heated to the required temperature before the addition of CO/Ethene to the required pressure. The catalysis was performed at 10 bar with 50/50 CO-ethylene at 80° C. for 2 h. The activity of the xylene and propylene backbone adamantyl compounds was compared. The results are collected in Table 2.

TABLE 2

Preliminary testing of adamantyl substituted catalysts

| Ligand | Weight gain | Product (by GC) |
|---|---|---|
| ―PAd$_2$ / ―PAd$_2$ (propylene) | 12.3 g | MeP |
| ortho-xylene PAd$_2$ / PAd$_2$ | 61.0 g | MeP |

Hence the xylene catalytic system is highly active and selective for MeP production essentially providing only one product by GC. An initial comparison with the 1,2-bis(di-tert-butylphosphinomethyl)benzene system in the autoclave was then performed, on an equimolar scale to the initial test under analogous conditions. However, the preformed catalysts [L^L]Pd(dba) were used with no excess ligand and the reactions carried out for 3 h. The results are collected in Table 3.

TABLE 3

Comparison of adamantyl and tert-butyl systems

| Ligand | Weight gain | Product (by GC) |
|---|---|---|
| PBu$^t_2$ / PBu$^t_2$ | 29.6 g | MeP |
| PAd$_2$ / PAd$_2$ | 75.7 g | MeP |

Under these conditions it appears that the adamantyl substituted catalyst is superior in activity/stability to the t-butyl catalyst.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings, or to any novel one, or any novel combination, of the steps of any method or process so disclosed.

The invention claimed is:

1. A catalyst system capable of catalysing the carbonylation of an olefinally unsaturated compound, which catalyst system is obtainable by combining:
   (a) a metal of Group VIB or Group VIIIB or a compound thereof: and
   (b) a bidentate phosphine of general formula (I)

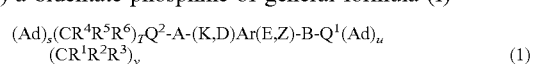

wherein:

Ar is a bridging group comprising an optionally substituted aryl moiety to which the phosphorus atoms are linked on available adjacent carbon atoms;

A and B each independently represent lower alkylene;

K, D, E and Z are substituents of the aryl moiety (Ar) and each independently represent hydrogen, lower alkyl, aryl, Het, halo, cyano, nitro, OR$^{10}$, OC(O)R$^{11}$, C(O)R$^{12}$, C(O)OR$^{13}$, NR$^{14}$R$^{15}$, C(O)NR$^{16}$R$^{17}$, C(S)R$^{16}$R$^{17}$, SR$^{18}$, C(O)SR$^{18}$, or -J-Q$^3$(Ad)$_w$(CR$^7$(R$^8$)(R$^9$))$_x$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, OR$^{10}$, OC(O)R$^{11}$, C(O)R$^{12}$, C(O)OR$^{13}$, NR$^{14}$R$^{15}$, C(O)NR$^{16}$R$^{17}$, C(S)R$^{16}$R$^{17}$, SR$^{18}$ or C(O)SR$^{18}$;

R$^1$ to R$^6$ each independently represent lower alkyl, aryl, or Het;

Ad each independently represent an optionally substituted adamantyl radical bonded to the phosphorous atom via any one of its tertiary carbon atoms, the said optional substitution being by one or more substituents selected from hydrogen, lower alkyl, halo, cyano, nitro, OR$^{10}$, OC(O)R$^{11}$, C(O)R$^{12}$, C(O)OR$^{13}$, NR$^{14}$R$^{15}$, C(O)NR$^{16}$R$^{17}$, C(S)R$^{16}$R$^{17}$, SR$^{18}$ or C(O)SR$^{18}$;

R$^{10}$ to R$^{18}$ each independently represent hydrogen, lower alkyl, aryl or Het;

S & U=0, 1 or 2 provided that S+U≧1;

T & V=0, 1 or 2 provided that T+V≦3;

W & X=0, 1 or 2;

Q$^1$, Q$^2$ and Q$^3$ (when present) each independently represent phosphorous, arsenic or antimony and in the latter two cases references to phosphine or phosphorous above should be varied accordingly.

2. A catalyst system according to claim 1 wherein, the Group VIII B metal is palladium.

3. A catalyst system according to claim 1, wherein $R^1$ to $R^9$ each independently represent lower alkyl, aralkyl or aryl.

4. A catalyst system according to claim 1, wherein $R^1$ to $R^9$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein).

5. A catalyst system according to claim 1, wherein each $Q^1$, $Q^2$ and $Q^3$ (when present) are the same.

6. A catalyst system according claim 1, each $Q^1$, $Q^2$ and $Q^3$ (when present) represents phosphorous.

7. A catalyst system according to claim 1, wherein A, B and J (when present) each independently represent $C_1$ to $C_6$ alkylene which is optionally substituted as defined herein, for example with lower alkyl groups.

8. A catalyst system according to claim 1, wherein when K, D, E or Z does not represent -J-$Q^3$(Ad)$_w$(CR$^7$(R$^8$)(R$^9$))$_x$, K, D, E or Z represents hydrogen, lower alkyl, phenyl or lower alkylphenyl.

9. A catalyst system according to claim 1, wherein when K, D, E and Z together with the carbon atoms of the aryl ring to which they are attached do not form a phenyl ring, K, D, E and Z each independently represent hydrogen, lower alkyl, phenyl or lower alkylphenyl.

10. A catalyst system according to claim 1, wherein when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, OR$^{10}$, OC(O)R$^{11}$, C(O)R$^{12}$, C(O)OR$^{13}$, NR$^{14}$R$^{15}$, C(O)NR$^{16}$R$^{17}$, SR$^{18}$, C(O)SR$^{18}$ or C(S)NR$^{16}$R$^{17}$ wherein R$^{10}$ to R$^{18}$ each independently represent hydrogen or lower alkyl (which alkyl group may itself be optionally substituted or terminated as defined herein).

11. A catalyst system according to claim 1, wherein $S \geq 1$ and $u \geq 1$.

12. A process for the carbonylation of an ethylenically unsaturated compound comprising contacting an ethylenically unsaturated compound with carbon monoxide and either water or an organic molecule having a hydroxyl functional group in the presence of a catalyst system in accordance with claim 1.

13. A process according to claim 12, wherein the organic molecule having a hydroxyl functional group may be branched or linear, and comprises an alkanol, particularly a $C_1$-$C_{30}$ alkanol, including aryl alkanols, which may be optionally substituted with one or more substituents selected from lower alkyl, aryl, Het, halo, cyano, nitro, OR$^{10}$, OC(O)R$^{11}$, C(O)R$^{12}$, C(O)OR$^{13}$, NR$^{14}$R$^{15}$, C(O)NR$^{16}$R$^{17}$, C(S)R$^{16}$R$^{17}$, SR$^{18}$ or C(O)SR$^{18}$ as defined herein.

14. A process according to claim 12, wherein the carbonylation of an ethylenically unsaturated compound is performed in one or more aprotic solvents.

15. A process according to claim 12, wherein the reaction is carried out in the absence of any external added aprotic solvent ie. an aprotic solvent not generated by the reaction itself.

16. A process according to claim 12, wherein the anion may be derived from or introduced as one or more of an acid having a pKa measured in aqueous solution at 18° C., of less than 4.

17. A process according to claim 12, wherein ethylenically unsaturated compound contains 2 to 30 carbon atoms.

18. A catalyst system according to claim 1, wherein the catalyst system includes in a liquid reaction medium a polymeric dispersant dissolved in a liquid carrier, said polymeric dispersant being capable of stabilising a colloidal suspension of particles of the group VI or VIIIB metal or metal compound of the catalyst system within the liquid carrier.

19. A catalyst system according to claim 1, wherein each of the groups R to R$^3$, R$^4$ to R$^6$ and R$^7$ to R$^9$ together independently may form cyclic structures such as 1-norbornyl or 1-norbornadienyl.

* * * * *